United States Patent
Kalinski et al.

[11] Patent Number: 6,047,826
[45] Date of Patent: Apr. 11, 2000

[54] PACKAGE TRAY FOR MENISCAL NEEDLE

[75] Inventors: Robert J. Kalinski, Milford; Gene W. Kammerer, East Brunswick, both of N.J.

[73] Assignee: Ethicon, Inc., Somerville, N.J.

[21] Appl. No.: 09/040,883

[22] Filed: Mar. 18, 1998

[51] Int. Cl.[7] .................................................. B65D 83/10
[52] U.S. Cl. .......................... 206/365; 206/438; 206/485
[58] Field of Search ................................... 206/363, 364, 206/365, 366, 438, 560, 564, 380, 443, 227

[56] References Cited

U.S. PATENT DOCUMENTS

| | | | |
|---|---|---|---|
| 3,768,635 | 10/1973 | Eggert | 206/366 |
| 4,006,747 | 2/1977 | Kronenthal et al. . | |
| 4,023,678 | 5/1977 | Fiedler | 206/363 |
| 4,349,022 | 9/1982 | Ishikawa . | |
| 4,929,427 | 5/1990 | Guala | 206/366 |
| 4,974,728 | 12/1990 | Colton . | |
| 5,031,775 | 7/1991 | Kane . | |
| 5,085,639 | 2/1992 | Ryan . | |
| 5,088,982 | 2/1992 | Ryan . | |
| 5,320,633 | 6/1994 | Allen et al. . | |
| 5,470,337 | 11/1995 | Moss . | |
| 5,492,671 | 2/1996 | Krafft | 206/363 |
| 5,848,693 | 12/1998 | Davis et al. | 206/438 |

FOREIGN PATENT DOCUMENTS

| | | |
|---|---|---|
| 8202850 | 12/1983 | Brazil . |
| 2 198 644 | 6/1988 | United Kingdom . |
| WO 92/12743 | 8/1992 | WIPO . |

*Primary Examiner*—Paul T. Sewell
*Assistant Examiner*—Luan K. Bui
*Attorney, Agent, or Firm*—Emil Richard Skula

[57] ABSTRACT

A package tray for arthroscopic H-fastener needles. The tray has a flexible base member having a central opening, and proximal and distal needle mounting members extending form the base member having slits and undercut engagement members for receiving and retaining the needles.

6 Claims, 3 Drawing Sheets

PACKAGE TRAY FOR MENISCAL NEEDLE

TECHNICAL FIELD

The field of art to which this invention relates is packaging, in particular, packaging for medical needles such as a meniscal repair needle.

BACKGROUND OF THE INVENTION

The use of H-type fasteners to repair tissue is known in the art. A device and H-fastener for repairing tissue are disclosed in U.S. Pat. No. 5,470,337. A method of repairing a meniscus in a knee using an H-fastener is disclosed in U.S. Pat. No. 5,320,633. A method of repairing tissue using H-fasteners is disclosed in U.S. Pat. No. 4,006,747.

In order to apply an H-fastener to a tissue site, a specially designed applicator is typically used. The applicator typically has a handle, a trigger mechanism connected to an actuation mechanism and a needle mounted to the distal end of the applicator. The needles typically have a hollow passage and a longitudinal slot for receiving H-fasteners. The needles may be straight or curved, and come in various sizes, depending upon the type of tissue which it is desired to approximate. One leg of the H-fastener is typically loaded into the slotted needle, and after penetration through tissue, the leg is ejected from the needle by the actuation mechanism after engaging the trigger.

There is a need in this art for a simple package for meniscal repair needles useful with H-fasteners which would accommodate a wide variety of needle shapes and sizes. There is also a need in this art for a package for such a needle which would assist the health care professional in mounting the needle to the applicator.

SUMMARY OF THE INVENTION

Therefore, it is an object of the present invention to provide a novel, flexible package tray for a medical needle used for H-fasteners which accommodates a variety of shapes and sizes of needles.

Another object of the present invention is to provide a package tray for a needle useful with an H-fastener applicator which protects the needle during shipping, handling and storage.

It is a further object of the present invention to provide a tray package for a medical needle used for H-fasteners which assists the health care provider in mounting the needle to an applicator.

Accordingly, a tray package for a medical needle is disclosed. The tray package has a flexible base member having a central opening. The base member has a proximal end and a distal end, and opposed sides. A first needle tip mounting member extends from the distal end of the base member adjacent to the opening. A needle attachment end mounting member extends from the proximal end of the base member adjacent to the opening. There is a slot in the needle attachment end mounting member having a bottom, opposed sides, a first open end, a second opposed open end, and an open top. There is also a slot in the needle tip mounting member having a bottom, opposed sides, an open top, a proximal open end, and a distal closed end. The slots in both the needle tip mounting member and the needle attachment mounting member have first and second opposed undercut members extending from the sides of the slots to assist in retaining the needle the slots.

Yet another aspect of the present invention is the above-described package having an opening on one side of the base member in communication with the central opening.

These and other aspects and advantages of the package trays of the present invention will become more apparent by the following description and accompanying drawings.

DESCRIPTION OF THE PREFERRED EMBODIMENT

Figure 1:
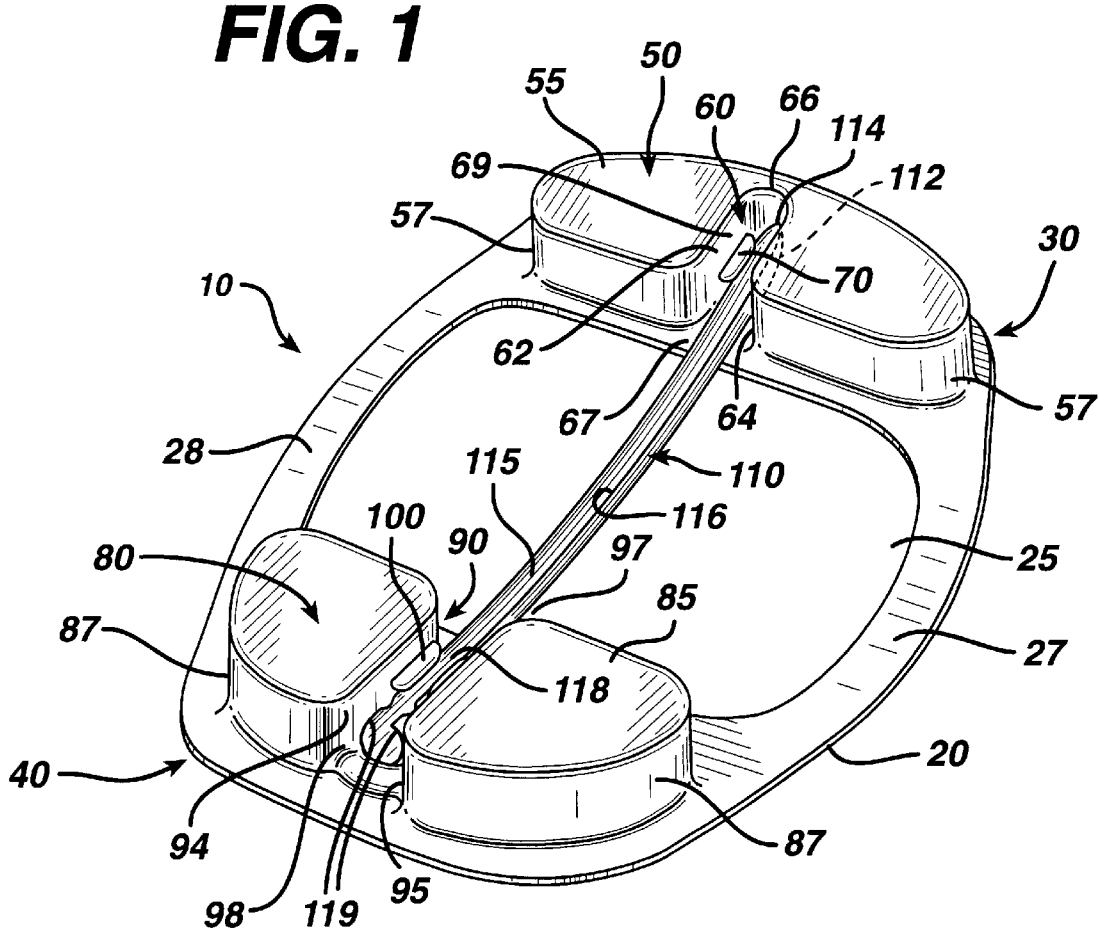
FIG. 1 is a perspective view of a tray package of the present invention containing a needle.
Figure 2:
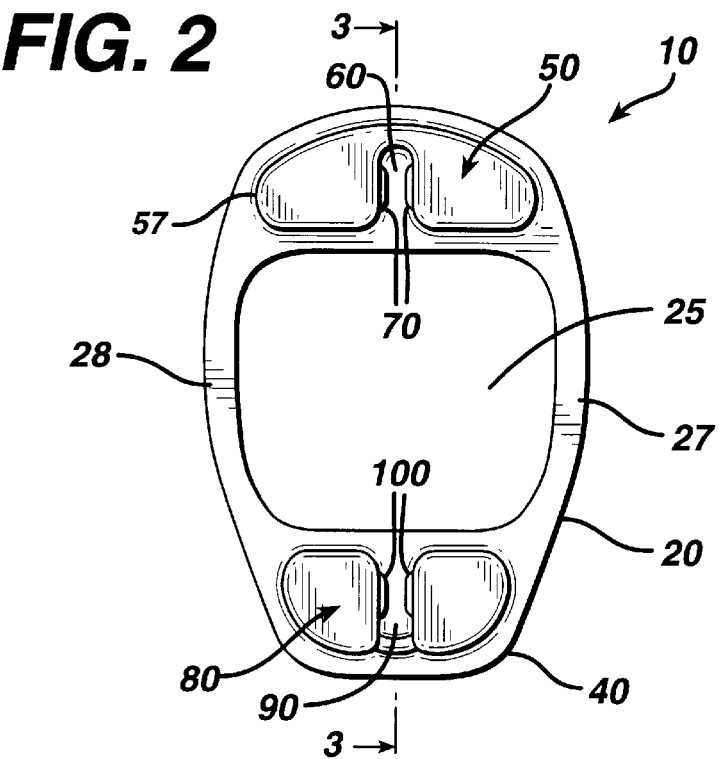
FIG. 2 is a plan view of the tray package of FIG. 1.
Figure 3:
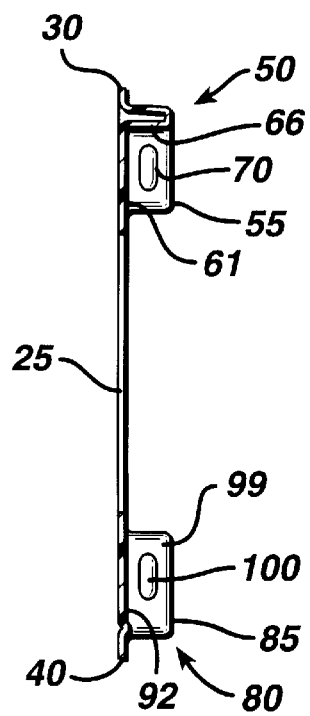
FIG. 3 is a side cross-sectional view taken along View Line 3—3 of the tray package of FIG. 2.

Referring to FIGS. 1, 2 and 3, a tray package of the present invention is seen. The tray package 10 is seen to have flexible, flat base member 20. Base member 20 is seen to have distal end 30 and proximal end 40. Base member 20 is seen to have central opening 25. The base member 20 is also seen to have opposed sides 27 and 28 adjacent to opening 25.

Extending upward from distal end 30 of base member 20 is needle tip mounting member 50. Member 50 is seen to have top 55 and sides 57. Contained in mounting member 50 is slot 60. Slot 60 is seen to have bottom 61, opposed sides 62 and 64, rounded distal end 66 and open proximal end 67. The slot 60 also is seen to have open top 69 extending through top 55 of member 50. Slot 60 is further seen to have a pair of opposed undercut members 70 extending from sides 62 and 64 into slot 60, preferably located midway above the bottom 61.

Extending upwardly from the proximal end 40 of base member 20 is the needle attachment end mounting member 80. Mounting member 80 is seen to have top 85 and sides 87. The attachment end mounting member 80 is seen to have slot 90. Slot 90 is seen to have bottom 92, opposed sides 94 and 95, opposed open ends 97 and 98, and open top 99 extending through the top 85 of attachment mounting end member 80. As illustrated in FIG. 1, it is desirable to bevel or round member 60 in the vicinity of the entrance open end 98 to facilitate mounting of the a needle to an applicator; in effect, this will help to guide the applicator to the mounting end of the needle. Slot 90 is further seen to have a pair of opposed undercut members 100 extending from sides 94 and 95 into slot 90.

As seen in FIG. 1, the curved needle 110 has pointed distal piercing end 112 having piercing tip 114, longitudinal passage 115, slot 116 and proximal mounting end 118 with mounting bayonets 119. The needle 110 is mounted in tray 10 by forcing distal needle end 112 into slot 60 below the undercut members 70. Then tray 10 is bent, or rotated upward, and the needle mounting end 118 is inserted into slot 90 beneath the undercut members 100. With a curved needle 110, the middle section of the needle body will tend to extend into opening 25. A straight needle to be mounted in package 10 will be mounted in a similar manner except that the base member 20 will not be bent.

Figure 4:
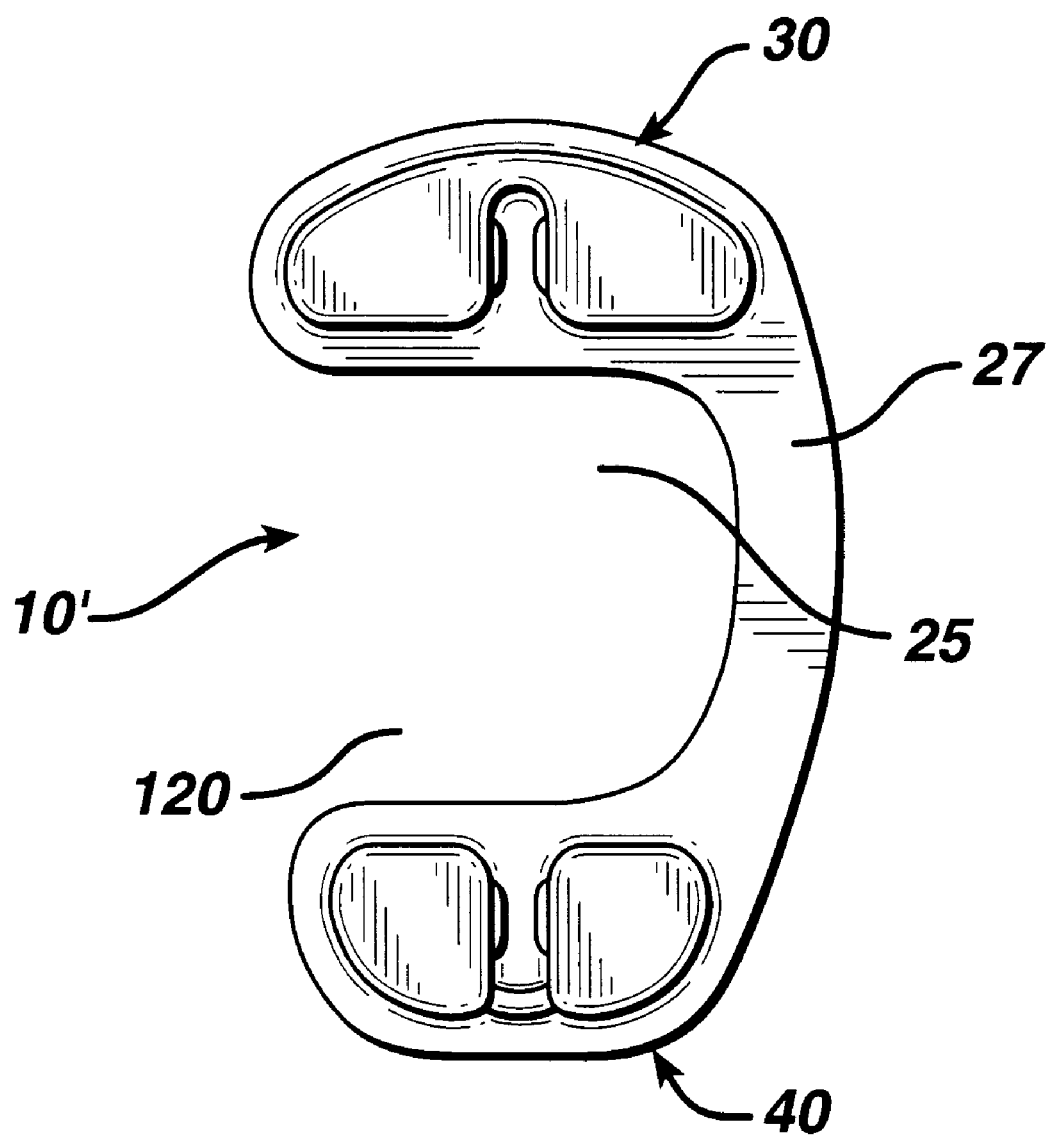
FIG. 4 is a plan view of an alternate embodiment of a tray package of the present invention wherein there is an opening in a side member in communication with the central opening.

An alternate embodiment of the package of the present invention is seen in FIG. 4. Package 10' is identical to the embodiment as illustrated in FIGS. 1, 2 and 3, except the package 10' of the alternate embodiment is seen to have side 28 removed, or alternatively an opening in side 28 is formed, so that a mouth 120 is formed in communication with opening 25 and only side 27 remains to connect distal end 30 with proximal end 40. It will be appreciated by those skilled in the art that the alternate embodiment package 10' is preferably manufactured without side 28, although package 10 can be modified by cutting away member 28, or a part thereof, to form the alternate embodiment package 10'.

The packages of the present invention will preferably be manufactured in a conventional manner using conventional equipment and processes such as thermoforming or injection molding. Preferably the packages of the present invention will be made from conventional polymers used in medical packaging such as polypropylene, polystyrene and polyethylene, and equivalents thereof. The packages 10 of the present invention containing needles 110 are preferably packaged in a conventional outer overwrap package such as a Tyvek envelope or foil package and then sterilized using conventional sterilization processes such as radiation, autoclaving, gaseous sterilants, and the like.

The packages of the present invention for H-fastener applicator needles are easy to manufacture and accommodate a variety of needle shapes and sizes. The packages of the present invention can accommodate straight or curved needles, needles of various lengths and needles having various diameters.

Although is invention has been shown and described with respect to detailed embodiments thereof, it will be understood by those skilled in the art that various changes in form and detail thereof may be made without departing from the spirit and scope of the claimed invention.

We claim:

1. A tray package for medical needle comprising:
   a flexible base member having a proximal end and a distal end, and opposed sides;
   a central opening in the base member;
   a needle tip mounting member extending from the distal end of the base member adjacent to the opening;
   a needle attachment end mounting member extending from the proximal end of the base member adjacent to the opening;
   a slot in the needle attachment end mounting member having a bottom, opposed sides, a first open end, a second opposed open end, and an open top;
   a slot in the needle tip mounting member having a bottom, opposed sides, an open top, a proximal open end, and a distal closed end; and,
   first and second opposed undercut members extending from the sides of the slot in needle tip and needle attachment end mounting members for retaining a needle in the slots.

2. The tray package of claim 1 further comprising a beveled entrance in the needle attachment end mounting member adjacent to the first open end.

3. The tray package of claim 1 wherein the distal closed end of the slot in the needle tip mounting member is rounded.

4. A tray package for medical needle comprising:
   a base member having a proximal end and a distal end, and opposed sides;
   a central opening in the base member;
   a mouth opening in one side of the base member in communication with the central opening;
   a needle tip mounting member extending from the distal end of the base member adjacent to the central opening;
   a needle attachment end mounting member extending from the proximal end of the base member adjacent to the central opening;
   a slot in the needle attachment end mounting member having a bottom, opposed sides, a first open end, a second opposed open end, and an open top;
   a slot in the needle tip mounting member having a bottom, opposed sides, an open top, a proximal open end, and a distal closed end; and,
   first and second opposed undercut members extending from the sides of the slot in needle tip and needle attachment end mounting members for retaining a needle in the slots.

5. The tray package of claim 4 further comprising a beveled entrance in the needle attachment end mounting member adjacent to the first open end.

6. The tray package of claim 4 wherein the distal closed end of the slot in the needle tip mounting member is rounded.

* * * * *